United States Patent [19]

Clynes

[11] Patent Number: 5,195,895
[45] Date of Patent: Mar. 23, 1993

[54] SENTIC CYCLER UNIT

[76] Inventor: Manfred Clynes, 19181 Mesquite Ct., Sonoma, Calif. 95476

[21] Appl. No.: 787,254

[22] Filed: Nov. 4, 1991

[51] Int. Cl.$^5$ ............................................. G09B 19/00
[52] U.S. Cl. .................................................. 434/236
[58] Field of Search ................................ 434/236, 319

[56] References Cited

U.S. PATENT DOCUMENTS

| | | | |
|---|---|---|---|
| 3,691,652 | 9/1972 | Clynes | 434/236 |
| 3,755,922 | 9/1973 | Clynes | 434/236 |
| 4,246,913 | 1/1981 | Ogden et al. | 434/236 X |
| 4,419,540 | 12/1983 | Henderson | 434/167 |
| 4,770,636 | 9/1988 | Buschke | 434/236 |
| 4,931,934 | 6/1990 | Snyder | 434/236 X |
| 5,079,726 | 1/1992 | Keller | 434/236 X |

*Primary Examiner*—Gene Mancene
*Assistant Examiner*—L. Thomas
*Attorney, Agent, or Firm*—Michael Ebert

[57] ABSTRACT

A self-sufficient sentic cycler unit usable by a subject to generate and express emotions as an art form of touch and in doing so to overcome inhibitive and repressive tendencies, and to relieve stress and dissipate anxiety. The unit includes a solid-state memory having digitally stored therein a set of words representing different emotions, such as love or anger, as well as a click or other command signal instructing the subject to tactilely express the emotion represented by the word selected from the memory. The memory is controlled by a clock and a programmed microprocessor to produce a sentic cycle in the course of which words are selected from the set in a predetermined sequence, each selected word being followed by a series of time-spaced clicks. The digital output of the memory is converted into an analog signal that is reproduced so that it can be heard by the subject. The unit is provided with a finger rest which is to be pressed by the subject who after hearing a selected word then hears a command click in the click series following the word. The subject, after hearing each click, then exerts finger pressure on the finger rest in a manner expressive of the emotion evoked by the word.

14 Claims, 1 Drawing Sheet

SENTIC CYCLER UNIT

BACKGROUND OF THE INVENTION

1. Field of Invention

This invention relates generally to a technique for evoking in a subject generalized emotional states which are each expressed in tactile terms in the course of a sentic cycle and give rise to an emotional release having beneficial effects, and more particularly to a sentic cycler unit for carrying out this technique, the unit including a programmed microprocessor associated with a solid-state memory in which a set of words representing different emotions are digitally stored and are sequentially reproduced in accordance with the program.

2. Status of Prior Art

A concern of the present invention is with the relief of stress and the dissipation of anxiety by affording a subject with a natural means for emotional expression without the need for acquiring specific skills to attain this end. The utility of the invention is not limited to distressed subjects, for it may be used to enhance the mental state of normal subjects. A study of human emotions from the biocybernetic standpoint may be found in the text, "Biomedical Engineering Systems," edited by Clynes and Milsum (McGraw-Hill—1970).

In studies reported in the above-identified text, the difficulties of measuring emotional characteristics quantitatively were overcome by normalizing expressions of emotion through measurement of touch-pressure transients in two dimensions produced by one finger of the subject, and by using internally-generated fantasized emotions. By requiring repetitive expressive acts for each emotion and averaging these acts on a computer, one derives from the transient pattern created by finger pressure, the expressive shape for the emotion generated through repetitive expressions.

The use of a single finger to produce an expressive shape assumes the existence of a basic brain program for the expression of a given emotion. It is, however, immaterial whether a finger, foot or other body part is used in the expression. The consistent results obtained with this measurement technique confirms this supposition.

My prior patent U.S. Pat. No. 3,755,922 (1973) discloses a system for producing a set of personalized sentograms constituting a personality relationship profile of a subject being diagnosed. This system includes a programmer in the form of a standard magnetic tape cassette player adapted to present to the subject a predetermined sequence of names, each identifying an individual with whom the subject has a close relationship or about whom the subject has distinct feelings. After a name is presented, the subject is commanded by a signal to express his feeling about the named individual by pressing with his finger a finger rest on a pressure-sensitive transducer to produce a transient wave form whose shape reflects this feeling. The shapes initiated by a series of command signals are averaged to created a personalized sentogram. The set of sentograms resulting from the sequence of names provides a personality relationship profile of the subject useful in diagnosis and prognosis. The present invention does not seek to provide sentograms but serves to employ the tactile expression of emotions for beneficial purposes. By evoking repetitive expressive acts for each emotion and averaging these acts on a computer, one derives from the transient pattern created by finger pressure, the expressive shape for the emotion.

The use of a single finger to produce an expressive shape assumes the existence of a basic brain program for the expression of a given emotion. It is, however, immaterial whether a finger, foot or other body part is used in the expression. The consistent results obtained with this measurement technique confirms this supposition.

My prior patent U.S. Pat. No. 3,755,922 (1973) discloses a system for producing a set of personalized sentograms constituting a personality relationship profile of a subject being diagnosed. This system includes a programmer in the form of a standard magnetic tape cassette player adapted to present to the subject a predetermined sequence of names, each identifying an individual with whom the subject has a close relationship or about whom the subject has distinct feelings. After a name is presented, the subject is commanded by a signal to express his feeling about the named individual by pressing with his finger a finger rest on a pressure-sensitive transducer to produce a transient wave form whose shape reflects this feeling. The shapes initiated by a series of command signals are averaged to created a personalized sentogram. The set of sentograms resulting from the sequence of names provides a personality relationship profile of the subject useful in diagnosis and prognosis. The present invention does not seek to provide sentograms but serves to employ the tactile expression of emotions for beneficial purposes.

Hence of greater relevance is my prior patent U.S. Pat. No. 3,691,652 (1972), where in order to enhance the ability of a subject to express emotions freely and to overcome his inhibitive and repressive tendencies, a system is provided for generating generalized emotional states by way of repeated random signal initiations and expressive touch. The subject goes through a programmed sequence of generalized states of emotion in the course of a sentic cycle whose duration is, say, 30 minutes. Such sentic cycles have been found to have a calming effect on the subject and to result in a lessening of stress and anxiety.

A more detailed analysis of sentic cycles is found in chapter 5 of the text "Emotion and Psychopathology," edited by M. Clynes and J. Panksepp, Plenum Press, New York 1988, this chapter being headed "Generalized Emotion, How It is Produced and Sentic Cycle Therapy." Appendix A in this chapter gives "Timings for The Start of Expressions for Sentic Cycles (soft clicks)."

As in my '922 patent, in the system disclosed in my '652 patent, the subject is called upon to express the quality of a sentic state given in a word approximation, such as love, hate, anger, grief, sex and reverence. This state is physically expressed by pressing a finger rest actuating a pressure-sensitive transducer whose output is converted to a sentic expressive transient shape exhibited on a TV screen or other visual indicator. In both of my patents, in order to present in sequence the words representing the emotions, each of which is followed by a command signal, use is made of a conventional magnetic tape cassette player.

The system disclosed in my prior '652 patent is relatively elaborate and costly, and by no means portable. Hence the subject, in order to obtain the benefit of the system, must attend a facility having the necessary equipment. This rules out the use by the subject of the system at home or at whatever other site suits his convenience and needs.

Inasmuch as a sentic cycler unit in accordance with the invention makes use of a microelectronic system having a solid-state memory to store the words and signals necessary for a sentic cycle, the following prior art patents are of background interest.

The Shirf et al. patent U.S. Pat. No. 3,803,535 and the DeSmet patent U.S. Pat. No. 4,884,974 both disclose solid-state devices in which words and sound effects are digitally stored in a read-only memory chip or ROM. A ROM is a non-volatile memory which once its discrete storage sites are loaded, the data stays therein even if the power is shut off. In order to load the ROM, spoken words and sound effects are first recorded to produce an audio waveform which is then sampled at a high sampling rate. Each sample is then digitized and stored as a binary value in a ROM site. Then in order to extract the stored sounds from the ROM and reconstruct the audio waveform, the stored digital values are read out from the ROM and fed in sequence as input signals to a digital-to-analog converter.

Message extraction from a ROM is effected by a start-of-message signal applied to an electronic clock which then generates a train of periodic clock pulses that are applied to a counter that causes the memory sites in the ROM where the digitized samples of the message are stored, to be read out in sequence. The digitized sample signals yielded by the ROM are fed to a D-to-A converter whose output is a stepped analog waveform. This is applied to a low-pass filter to smooth out the transitions in the stepped wave to produce an audio signal resembling the original audio signal. This audio signal is amplified and reproduced so that it can be heard by the user.

Also of background interest are the following publications:

Methodology in Sentographic Measurement of Motor Expression of Emotion: Two-Dimensional Freedom of Gesture Essential" by Clynes in Perceptual and Motor Skills, 1989, 68 779–183.

"Inherent Cognitive Substrates of Specific Emotions: Love is Blocked by Lying but Not Anger," by Clynes and Ryan in Perceptual and Motor Skills, 1990, 70 195–206.

"Some Guidelines for the Synthesis and Testing of by Clynes in Music Perception, Summer 1990, Vol. 7, No. 4, 403–422.

SUMMARY OF INVENTION

The main object of this invention is to provide a self-sufficient sentic cycler unit adapted in the course of a sentic cycle to evoke in a subject a series of generalized emotional states which are each expressed in tactile terms and gives rise as with music to an emotional release having beneficial effects.

A significant advantage of a sentic cycler unit in accordance with the invention as compared to the system disclosed in my prior '922 patent is that it is highly compact and portable, and may be used by a subject at home or whatever other site suits his convenience and needs. Another advantage of this unit is that it does away with the need to visually represent sentic waveforms, for these waveforms play no role in obtaining an emotional release.

More specifically, an object of this invention is to provide a battery-powered sentic cycler unit constituted by a programmed microprocessor associated with a solid-state memory, so that the unit may be used at any site, whether or not a power source is there available.

Yet another object of this invention is to provide a sentic cycler unit in which each reproduced word derived from the memory representing a particular emotion is followed by a series of time-spaced command signals or clicks instructing the subject to exert finger pressure on a finger rest in a manner expressing this emotion, whereby the subject continues to express this emotion in response to each click in the series.

A salient feature of the invention resides in a unit having two button controls, one of which when actuated at some point in the series of time-spaced clicks following a particular reproduced word, causes the sentic cycler unit to revert to the first click in the series, whereby the subject can then repeatedly express the same emotion for an additional number of times. The second button, when actuated at some point in the series of clicks, causes the unit to skip over the remaining clicks in the series and to reproduce the next word in the sequence. And if the second button is actuated at the end of a sentic cycle, the entire cycle is repeated.

Also an object of the invention is to provide a highly compact unit which operates efficiently and reliably and can be mass produced at low cost so that its therapeutic benefits can be made widely available.

Briefly stated, these objects are attained in a self-sufficient sentic cycler unit usable by a subject to generate and express emotions as an art form of touch, and in doing so to overcome inhibitive and repressive tendencies, and to relieve stress and dissipate anxiety. The unit includes a solid-state memory having digitally stored therein a set of words representing different emotions, such as love or anger, as well as a click or other command signal instructing the subject to tactilely express the emotion represented by the word selected from the memory. The memory is controlled by a clock and a programmed microprocessor to produce a sentic cycle in the course of which words are selected from the set in a predetermined sequence, each selected word being followed by a series of time-spaced clicks.

The digital output of the memory is converted into an analog signal that is reproduced so that it can be heard by the subject. The unit is provided with a finger rest which is to be pressed by the subject who after hearing a selected word then hears a command click in the click series following the word. The subject, after hearing each word, then exerts finger pressure on the finger rest in a manner expressive of the emotion evoked by the word.

BRIEF DESCRIPTION OF DRAWINGS

For a better understanding of the invention as well as other objects and further features thereof, reference is made to the following detailed description to be read in conjunction with the accompanying drawing, wherein.

DESCRIPTION OF INVENTION

The Unit

Figure 1:
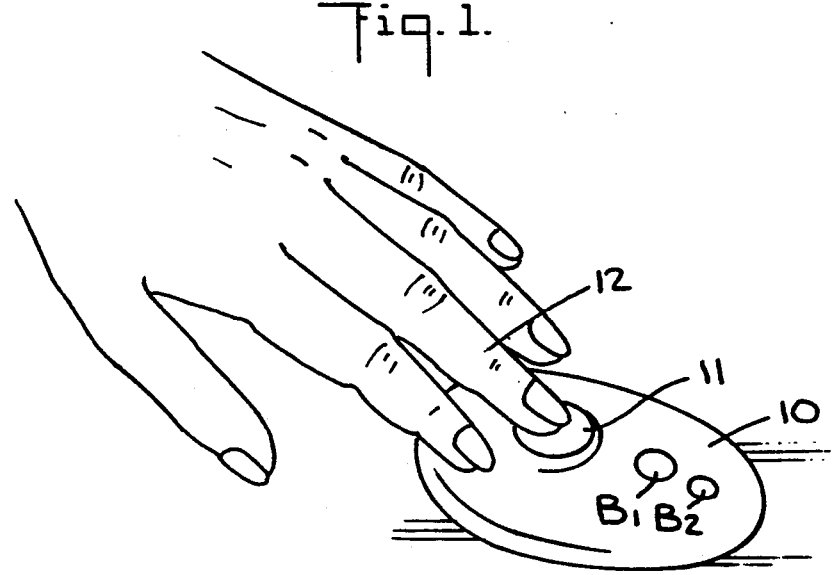
FIG. 1 is a perspective view of a sentic cycler unit in accordance with the invention.

Referring now to FIG. 1, there is shown a preferred embodiment of a sentic cycler unit in accordance with the invention. The unit is housed in a shallow casing molded of synthetic plastic material of high-strength, such as polypropylene or nylon. The casing has the shape of a flattened egg and is so compact that it can be clutched in one hand. Casing 10 is formed of separable complementary lower and upper sections which can be pried apart to permit batteries to be loaded therein.

Integral with the upper section of casing 10 at about its center is a raised finger rest 11. Rest 11 is provided at its central zone with a region formed of a slightly elastomeric or "giving" material. Hence when this region is engaged by the ball of a finger of the subject, such as the middle finger 12 shown in FIG. 1, this region yields somewhat when subjected to heavy pressure. In this way, the subject receives the impression that the finger rest is responsive to the applied pressure. The manner in which finger pressure is applied and the degree of pressure reflects the emotion expressed by the subject in relation to the selected word. The pressure pattern is generally consistent in response to a given word, but it differs from word to word. Thus the degree of finger pressure and how it is applied to the finger rest to physically express the emotion for the word "love" will be quite different from that applied to the finger rest to express the emotion "hate."

The upper section is also provided with buttons or touch-sensitive switches $B_2$ and $B_2$ whose function will be later described. These buttons are adjacent the fingers of the subject so that they may be actuated by a finger other than the one then engaging the finger rest. The sentic cycler unit is also provided with a small loudspeaker, say, of a one-inch diameter, from which is heard in sequence during the course of each sentic cycle emotion-representing words such as "love," "hate," or "anger," each word being followed by a series of time-spaced clicking sounds or other command signals instructing the subject to express by finger pressure the emotion evoked by the selected word.

The speaker may be mounted on the lower section of the casing facing the supporting surface on which the unit rests. The lower section is provided at its undersurface with cushioning pads or feet which also serve to prevent the unit from sliding on this surface.

In practice, it is best that the subject make use of the sentic cycler unit in a sitting position, and for this purpose the compact unit can be placed on a coffee table, or on the armrest of a chair. Also, instead of a loudspeaker, an outlet jack may be provided for earphones.

The System

Figure 2:
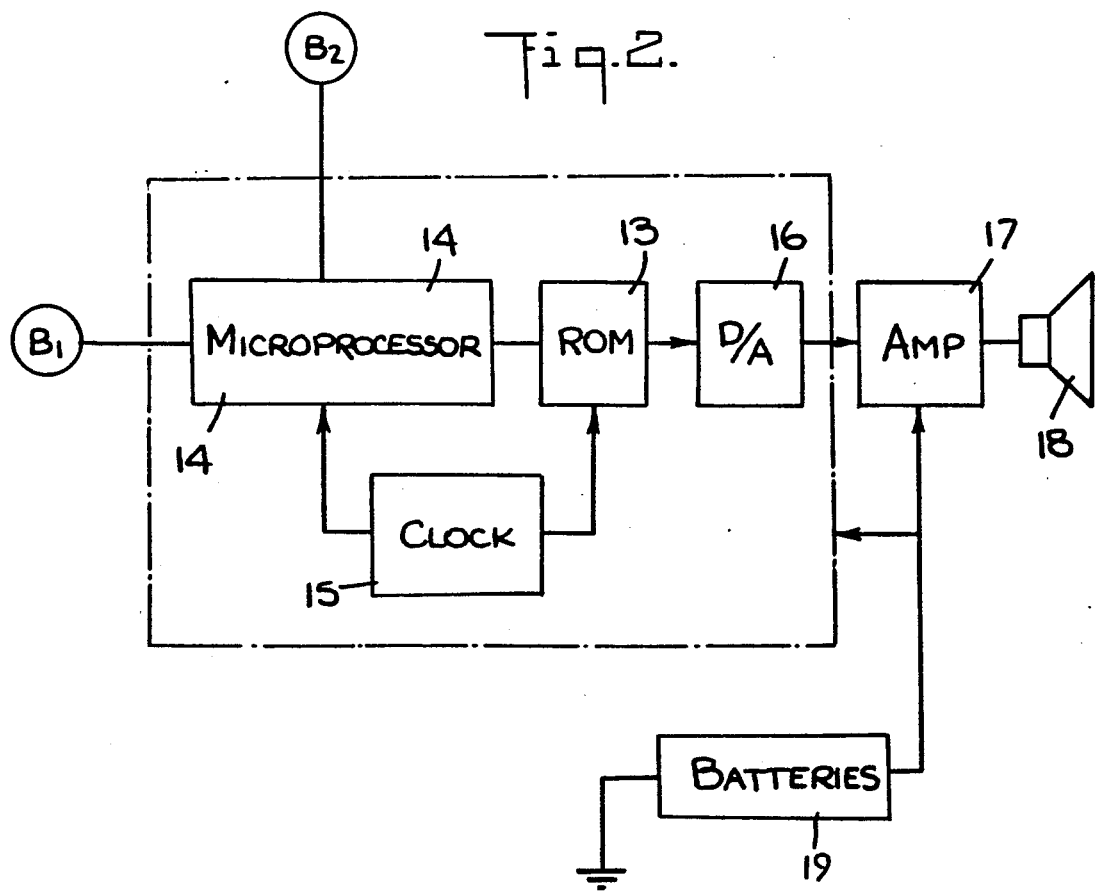
FIG. 2 is a block diagram of the microelectronic system included in the unit.

Referring now to FIG. 2 showing the microelectronic system included in the unit, it will be seen that the system includes a read-only-memory ROM 13. Digitally stored in ROM 13 are the set of words required for a sentic cycle lasting about 30 minutes, typically, "no emotion," "anger," "hate," "grief," "love," "sex," "joy" and "reverence." Also digitally stored in ROM 13 is the sound of a command click such as that produced by a soft knock on a piece of wood or any other abrupt sound signal acting to command the subject to apply finger pressure to the finger rest to physically express the emotion the subject feels that is represented by the selected word in the sequence.

ROM 13 is controlled by a microprocessor 14 associated with an electronic clock 15. A microprocessor is a central control unit on a single integrated circuit chip. Each microprocessor has its own architecture which encompasses the general layout of its major components. These components, which constitute the hardware of the microprocessor, include a program counter, a register, an arithmetic/logic unit, bus control and an internal memory or stack. Besides the hardware is the instruction set or software, the program of which takes the form of a set of logically related instructions stored in the internal memory of the microprocessor.

The program of microprocessor 14, as governed by clock 15, is such as to extract at predetermined times from ROM 13 in the course of each sentic cycle, successive words in the word set digitally stored in the ROM, each word being followed by a series of time-spaced clicks to command the subject to respond to the previously extracted word. The digital output of ROM 13 is converted by a D-to-A converter 16 into a corresponding analog signal. This analog signal, which is in stepped form, after suitable filtering, is applied to an amplifier 17 whose output is fed to a loudspeaker 18. Thus the subject in the course of a sentic cycle hears each word selected from the set, and after each word, the subject hears at spaced intervals the series of command clicks.

In practice, ROM 13, microprocessor 14, clock 15 and D/A converter 16 may be integrated into a single chip. Typically, this chip can be an ESS 3000 chip or one similar thereto. The unit is powered by a battery pack 19 preferably made up of AAA cells of the alkaline type or of the rechargeable nickel cadmium type.

The time spacing between clicks in a series thereof are preferably different for each emotion, but are distributed around a mean time appropriate for each emotion in a range of 4 to 10 seconds. The number of clicks in the series thereof following each word representing an emotion also varies from emotion to emotion in the sentic cycle sequence, but lies in a range of about 20 to 40 clicks per series.

The function of buttons $B_1$ and $B_2$ will now be explained. Both buttons or touch-sensitive switches are associated with microprocessor 14. When button $B_1$ is actuated in the course of a series of time-spaced clicks that follows the reproduction of a word in the sequence, the system then reverts to the first click in the series. This action gives the subject an additional number of clicks to express the emotion represented by the preceding word.

Thus if the word is "love," and button $B_1$ is actuated after the subject has already responded to 12 clicks in a series of 20, then the subject will now hear a series of 20 clicks; hence the total number of clicks following the word "love" is 32. In this way, the subject can prolong a particular emotion-response phase for as long as he desires. This freedom to prolong a given phase is useful to a subject who may feel that he or she on a particular occasion needs more time to express and enjoy a specific emotion.

In other instances, the subject may feel that in repeatedly expressing a particular emotion in response to the series of clicks following the word representing this emotion, that this expression has been sufficient when expressing this emotion, say, to the 12th click in a 20 click series, or the subject may not wish, on this occasion, to express, say, hate, or he may be pressed for time. The subject may then wish to skip the remaining clicks in the series and go on to the next word in the sequence. This skipping action is effected by actuating button $B_2$ which, when pressed, causes the microprocessor to read out from ROM 13 the next word in the sequence.

Button $B_2$ can also be used to effect a repeat of the entire sentic cycle. By pressing button $B_2$ at the conclusion of a sentic cycle, it will cause the microprocessor to read out from ROM 13 the first word in the sentic cycle sequence, causing the unit to repeat the cycle.

It has been found that at the completion of a sentic cycle, that the catharsis resulting from expressing a spectrum of emotions serves to relax the subject and to relieve his tensions without, however, diminishing his energy level. Indeed, it may heighten this level. Because the subject, who has had the benefit of the sentic cycle, is then substantially free of stress and anxiety, he is able to sleep better. Moreover, the subject, by continuing to use the unit over a period of weeks, learns to get in touch with the full range of his emotions and to discriminate among emotions and thereby relate more effectively with others in a more natural fashion.

The sentic cycler unit does not indicate or measure the dynamic sentic shapes evoked by the subject, nor does it indicate how well the subject has performed, for these are irrelevant to the beneficial function of the unit.

To render the unit usable universally, stored in the ROM are the seven to nine or more words in the set which normally make up a sentic cycle given in several languages, such as English, French, German, Russian, Japanese, Spanish and Italian. The ROM selected for this purpose must, of course, have a sufficient storage capacity for storing all of the words in the set in several languages. In this arrangement, the microprocessor must be associated with a language-selector switch or other enabling device.

Each click has a duration of 5 to 25 milliseconds, and the silent intervals between clicks are typically 4 to 10 seconds. Thus the unit has a very small duty cycle, for it is silent more than 99 percent of the time. The unit therefore consumes relatively little power and is operable for a prolonged period before it becomes necessary to replace or recharge the batteries.

Typically, the feeling of well being and calm imparted to the subject by the sentic cycler unit will last about 24 hours. It is recommended, therefore, that the subject use the unit three to five times a week. Under periods of stress, more frequent use may be desirable.

While stress relief and the dissipation of anxiety are obtained through the unit, it is also beneficial to those individuals who are relatively free of stress, for it enhances their sense of well being. Because the unit weighs only a few ounces and is highly compact, it can easily be carried in a pocket or purse.

An individual's ability to mentally control certain of his physiological functions such as body temperature or blood pressure is known as self-regulation. But with the exception of those committed to transcendental meditation, self-regulation techniques have not been widely practiced in Western society, possibly because many disorders induced or aggravated by stress which lend themselves to alleviation by self-regulation can more readily be treated by medication. Thus a tension headache as well as a migraine (a vascular headache more painful than a tension headache) can, to some degree, be relieved by aspirin and other drugs. Such medication does not, however, do away with stress factors responsible for the headache but serves only to moderate the symptoms. Moreover, aspirin and other drugs, when taken frequently and in large doses, often have deleterious side effects.

Emotional feelings are reflected in physiological activity. When an individual is angry, this feeling may be accompanied by changes in pulse rate, blood pressure and body temperature, and also by reactive physical movements. Thus an angry individual often clenches his fist.

In the context of a sentic cycler unit in accordance with the invention, anger is physically expressed by finger pressure imposed on the finger rest. And one reason the unit acts to relieve stress and have a calming effect on the subject is that an emotion such as anger is not suppressed but is released in the form of finger pressure.

However, anger is but one of several primary emotions, and with the sentic cycler unit, a spectrum of emotions is traversed in the course of each sentic cycle, both positive and negative.

A sentic cycler unit of the above-described type is passive in the sense that when a subject responds to a command click by applying finger pressure to the finger rest, apart from a slight yielding of the rest, the unit does not otherwise react to the applied pressure. The reaction which does occur takes place in the consciousness of the subject as he experiences an emotion evoked by the selected word and expresses this emotion by a finger action.

In order, therefore, to render the unit interactive, one may associate with the finger rest a pressure-sensitive switch which is actuated whenever the rest is pressed by the subject's finger, regardless of the degree of applied pressure. This switch is coupled to the microprocessor, and the system is so arranged that when a command click is heard following a selected word, and the subject then applies finger pressure to the rest to express the emotion represented by the word, the subject then hears a musical tone, phrase, chord or sound expressive of this emotion. Alternatively, the click itself may initiate the emotional sound.

Thus if the selected word is "grief," the musical tone then produced could be a dark cello sound suggestive of grief. And if the selected word is "love," then an appropriate musical phrase could be a soft violin sound, while for the word "anger," a growling tone produced by a tuba could be used. All of these sounds could be expressed with characteristic sentic forms (See: Clynes '773 and '992 patents).

The purpose of this musical sound is to create an aural environment serving to induce in the subject an emotional feeling appropriate to the selected word. The set of musical tones, phrases, chords or other sounds appropriate to the spectrum of words representing emotions are also stored in the ROM, and the microprocessor is programmed to respond to the finger rest switch action by extracting from the ROM the sound expression appropriate to the particular emotion to be then expressed by the subject upon hearing the command click following the selected word. The duration of the tones preferably corresponds to major portions of the intervals between command clicks so that the tones are played during the series of clicks following the selected word. The sounds so produced may be provided with every second or third touch expression, rather than with every single touch expression.

Art Form of Touch

With a sentic cycler unit in accordance with the invention, as the subject continues to use the unit, he can in doing so develop his own artistic touch, for the manner in which he presses the finger rest depends on his emotional feelings and how they are translated into finger motion. In developing and applying his own "touch," the subject will in this process gain measure of aesthetic satisfaction and improve the communication of feelings to others.

The practice of sentic cycles may therefore be regarded as a simple art form of touch. The sequence and timing of emotions and their expressions is given—this representing the composition. However, the emotions are not those of a composer, but those of the individual who practices the art form of touch. Improvisatory and spontaneous expressiveness and thought are combined with a program or metastructure (the series and duration of each emotion phase).

This art form of touch resides in the discovery, by each person, of the most appropriate and effective dynamic form of expressing an emotion, and sensing how that expression generates the emotion. Having found and sensed this, the person can then apply it to other situations and modes, thereby increasing the "livingness" (to use Susan Langer's term) of their communication and experience, and become more authentic.

This art teaches an individual how easily he or she can switch from one emotion to another, at will, and how such a sequence of emotions results in an overall impression greater than the sum of the parts. It impresses on the person how emotions are embedded in time, how time is part of the expression, communication and experience of emotion. And finally it can teach also how we may "consider" emotion and its quality, without becoming totally involved bodily, so that its timeless aspects are also perceived, as an existential entity.

In this (seemingly uniquely human) mode, called Apollonian (as distinguished from the more usual Dionysian mode), it becomes possible also to view the cognitive substrates of each emotion and become cognizant of them free from the constraints experienced in everyday life. Like other true art forms, the art form of touch is conducive to empathy and compassion. But unlike the visual and musical arts, the touch art of sentic cycles can be effectively learned in a relatively short period.

While there has been shown and described a preferred embodiment of a sentic cycler unit in accordance with the invention, it will be appreciated that many changes and modifications may be made therein without, however, departing from the essential spirit thereof.

I claim:

1. A sentic cycler unit provided with a finger rest engageable by a finger of a subject, said unit incorporating therein a microelectronic system comprising:
   (a) a solid-state memory having digitally stored therein data constituted by a set of words representing different emotions and a click or other command signal instructing the subject to then express by finger pressure exerted on said rest, the emotion represented by a word selected by said set;
   (b) a programmed microprocessor controlling the memory to produce a sentic cycle in the course of which the words are extracted from the set in a predetermined sequence, each extracted word being followed by a series of time-spaced clicks, the time spacing between the clicks in the series thereof following a given work in the set depending on the emotion represented by the word, whereby the data extracted from the memory takes the form of a digital signal; and
   (c) means to convert the digital signal into an analog signal and to reproduce the analog signal so that it can be heard by the subject who after hearing a selected word, upon then hearing each click in the series, exerts finger pressure on the rest to physically express the emotion represented by the word.

2. A unit as set forth in claim 1, wherein said memory is a read-only-memory.

3. A unit as set forth in claim 1, wherein said microprocessor and said memory are associated with an electronic clock which provides timing pulses for producing the sentic cycle.

4. A unit as set forth in claim 1, wherein said means to convert are constituted by a digital-to-analog converter whose output is fed through an amplifier to a loudspeaker.

5. A unit as set forth in claim 1, wherein said system is housed in a casing on whose upper surface is said finger rest.

6. A unit as set forth in claim 5, wherein said rest has a zone yieldable to pressure.

7. A unit as set forth in claim 5, wherein said casing is shallow and is molded of synthetic plastic material, the casing being formed by complementary upper and lower sections, the finger rest being integral with the upper section.

8. A unit as set forth in claim 1, wherein said microprocessor is programmed to produce for each word in the set a series of time-spaced clicks, the number of clicks in each series depending on the related word.

9. A unit as set forth in claim 8, wherein said number is at least twenty.

10. A unit as set forth in claim 9, wherein the time spacing between clicks is at least three seconds.

11. A unit as set forth in claim 1, further including a first control switch coupled to the microprocessor which is programmed so that when this switch is actuated after a click is heard whose time position is intermediate the first and last click in the series, the system then reverts to the first click to provide an additional number of clicks.

12. A unit as set forth in claim 1, further including a second control switch coupled to the microprocessor which is so programmed that when this switch is actuated after a click is heard whose time position is intermediate the first and last click in the series following a selected word, the system then skips over the remaining clicks in the series and acts to present the next word in the sequence.

13. A unit as set forth in claim 1, further including means to produce a sound expressive of the emotion represented by the selected word when the subject applies pressure to the finger rest.

14. A unit as set forth in claim 1, further including means to produce a sound expressive of the emotion represented by the selected word, when a click is produced following the word.

* * * * *

UNITED STATES PATENT AND TRADEMARK OFFICE
CERTIFICATE OF CORRECTION

PATENT NO. : 5,195,895
DATED : March 23, 1993
INVENTOR(S) : Manfred Clynes

It is certified that error appears in the above-indentified patent and that said Letters Patent is hereby corrected as shown below:

Column 9, line 59, claim 1, delete "work" and substitute --word--.

Signed and Sealed this

Fourth Day of January, 1994

Attest:

BRUCE LEHMAN

*Attesting Officer*  *Commissioner of Patents and Trademarks*